US009814684B2

(12) United States Patent
Castan et al.

(10) Patent No.: US 9,814,684 B2
(45) Date of Patent: *Nov. 14, 2017

(54) ORAL PHARMACEUTICAL FORMULATION IN THE FORM OF AQUEOUS SUSPENSION FOR MODIFIED RELEASE OF ACTIVE PRINCIPLE(S)

(71) Applicant: FLAMEL IRELAND LIMITED, Dublin (IE)

(72) Inventors: Catherine Castan, Orlienas (FR); Florence Guimberteau, Montussan (FR); Rémi Meyrueix, Lyons (FR)

(73) Assignee: FLAMEL IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/848,699

(22) Filed: Sep. 9, 2015

(65) Prior Publication Data

US 2015/0374636 A1    Dec. 31, 2015

Related U.S. Application Data

(63) Continuation of application No. 13/014,137, filed on Jan. 26, 2011, which is a continuation of application No. 10/510,643, filed as application No. PCT/US03/01096 on Apr. 7, 2003, now Pat. No. 7,906,145.

(30) Foreign Application Priority Data

Apr. 9, 2002 (FR) ..................... 02 04409
Sep. 2, 2002 (FR) ..................... 02 10847

(51) Int. Cl.
| A61K 9/50 | (2006.01) |
| A61K 9/10 | (2006.01) |
| A61K 9/00 | (2006.01) |
| A61K 31/155 | (2006.01) |
| A61K 31/192 | (2006.01) |
| A61K 31/522 | (2006.01) |
| A61K 31/585 | (2006.01) |
| A61K 31/43 | (2006.01) |

(52) U.S. Cl.
CPC .......... *A61K 9/5047* (2013.01); *A61K 9/0053* (2013.01); *A61K 9/10* (2013.01); *A61K 9/5015* (2013.01); *A61K 9/5026* (2013.01); *A61K 9/5042* (2013.01); *A61K 31/155* (2013.01); *A61K 31/192* (2013.01); *A61K 31/43* (2013.01); *A61K 31/522* (2013.01); *A61K 31/585* (2013.01)

(58) Field of Classification Search
None
See application file for complete search history.

(56) References Cited

U.S. PATENT DOCUMENTS

| 3,864,483 A | 2/1975 | Stein et al. |
| 3,892,769 A | 7/1975 | Shen et al. |
| 3,914,414 A | 10/1975 | Stein et al. |
| 3,914,415 A | 10/1975 | Stein et al. |
| 3,927,216 A | 12/1975 | Witkowski et al. |
| 3,966,917 A | 6/1976 | Prasad et al. |
| 3,980,766 A | 9/1976 | Shaw et al. |
| 4,029,884 A | 6/1977 | Stein et al. |
| 4,070,494 A | 1/1978 | Hoffmeister et al. |
| 4,308,251 A | 12/1981 | Dunn et al. |
| 4,321,253 A | 3/1982 | Beatty |
| 4,351,337 A | 9/1982 | Sidman |
| 4,434,153 A | 2/1984 | Urquhart et al. |
| 4,443,549 A | 4/1984 | Sadowski |
| 4,450,150 A | 5/1984 | Sidman |
| 4,454,309 A | 6/1984 | Gould et al. |
| 4,461,759 A | 7/1984 | Dunn |
| 4,486,471 A | 12/1984 | Samejima et al. |
| 4,572,912 A | 2/1986 | Yoshioka et al. |
| 4,639,436 A | 1/1987 | Junge et al. |
| 4,693,896 A | 9/1987 | Wheatley et al. |
| 4,728,512 A | 3/1988 | Mehta et al. |
| 4,748,023 A | 5/1988 | Tamas et al. |
| 4,833,905 A | 5/1989 | Hill |
| 4,892,738 A | 1/1990 | Takagishi et al. |
| 4,894,240 A | 1/1990 | Geoghegan et al. |
| 4,902,513 A | 2/1990 | Carvais |
| 4,904,769 A | 2/1990 | Rauenbusch |
| 4,961,932 A | 10/1990 | Theeuwes |
| 4,999,189 A | 3/1991 | Kogan et al. |
| 5,028,434 A | 7/1991 | Barclay et al. |
| 5,045,321 A | 9/1991 | Makino et al. |

(Continued)

FOREIGN PATENT DOCUMENTS

| CA | 2068366 A1 | 11/1992 |
| DE | 2 213 180 A1 | 9/1972 |

(Continued)

OTHER PUBLICATIONS

U.S. Appl. No. 11/439,432, filed May 24, 2006, Florence Guimberteau et al.

(Continued)

*Primary Examiner* — Robert A Wax
*Assistant Examiner* — Caralynne Helm
(74) *Attorney, Agent, or Firm* — Porzio, Bromberg & Newman P.C.

(57) ABSTRACT

The invention relates to liquid pharmaceutical formulations for oral administration with the modified release of active principle(s), excluding amoxicillin, said formulations consisting of suspensions of coated particles of active principles (microcapsules). According to the invention, the microcapsules constituting the disperse phase of the suspension are designed to allow the modified release of the active principle(s) according to a profile that does not change during the storage of the liquid suspension. To do this the inventors propose the selection of a specific coating composition for the microcapsules which consists of at least four components that allow these microcapsules to be stored in water without modifying their properties of modified release of the active principle, this liquid phase furthermore being saturated with active principle(s).

31 Claims, 2 Drawing Sheets

(56) References Cited

U.S. PATENT DOCUMENTS

| | | |
|---|---|---|
| 5,084,278 A | 1/1992 | Mehta |
| 5,091,485 A | 2/1992 | Noireaux et al. |
| 5,158,636 A | 10/1992 | Groitzsch et al. |
| 5,186,930 A | 2/1993 | Kogan et al. |
| 5,206,030 A | 4/1993 | Wheatley et al. |
| 5,219,895 A | 6/1993 | Kelman et al. |
| 5,248,516 A | 9/1993 | Wheatley et al. |
| 5,268,182 A | 12/1993 | Brinker et al. |
| 5,272,137 A | 12/1993 | Blase et al. |
| 5,286,495 A | 2/1994 | Batich et al. |
| 5,286,497 A | 2/1994 | Hendrickson et al. |
| 5,409,709 A | 4/1995 | Ozawa et al. |
| 5,409,711 A | 4/1995 | Mapelli et al. |
| 5,431,922 A | 7/1995 | Nicklasson |
| 5,445,829 A | 8/1995 | Paradissis et al. |
| 5,449,513 A | 9/1995 | Yokoyama et al. |
| 5,464,632 A | 11/1995 | Cousin et al. |
| 5,464,807 A | 11/1995 | Claude et al. |
| 5,472,704 A | 12/1995 | Santus et al. |
| 5,510,103 A | 4/1996 | Yokoyama et al. |
| 5,571,533 A | 11/1996 | Santus et al. |
| 5,589,455 A | 12/1996 | Woo |
| 5,594,016 A | 1/1997 | Ueno et al. |
| 5,603,957 A | 2/1997 | Burguiere et al. |
| 5,609,872 A | 3/1997 | Ahlborg et al. |
| 5,651,990 A | 7/1997 | Takada et al. |
| 5,656,295 A | 8/1997 | Oshlack et al. |
| 5,674,529 A | 10/1997 | Marder et al. |
| 5,674,533 A | 10/1997 | Santus et al. |
| 5,695,784 A | 12/1997 | Pollinger et al. |
| 5,750,468 A | 5/1998 | Wright et al. |
| 5,773,029 A | 6/1998 | Chiesi et al. |
| 5,780,055 A | 7/1998 | Habib et al. |
| 5,780,579 A | 7/1998 | Soula et al. |
| 5,804,573 A | 9/1998 | Silver |
| 5,846,566 A | 12/1998 | Burguiere et al. |
| 5,854,270 A * | 12/1998 | Gambhir ............ A61K 31/4178 514/397 |
| 5,858,398 A | 1/1999 | Cho |
| 5,904,936 A | 5/1999 | Huille et al. |
| 5,922,769 A | 7/1999 | Barelli et al. |
| 5,945,123 A | 8/1999 | Hermelin |
| 5,981,761 A | 11/1999 | Chou et al. |
| 6,022,562 A | 2/2000 | Autant et al. |
| 6,033,687 A | 3/2000 | Heinicke et al. |
| 6,068,859 A | 5/2000 | Curatolo et al. |
| 6,077,544 A | 6/2000 | Debregeas et al. |
| 6,099,862 A | 8/2000 | Chen et al. |
| 6,177,187 B1 | 1/2001 | Niemoller et al. |
| 6,179,862 B1 | 1/2001 | Sawhney |
| 6,180,141 B1 | 1/2001 | Lemercier et al. |
| 6,184,220 B1 | 2/2001 | Turck et al. |
| 6,221,377 B1 | 4/2001 | Meyer |
| 6,228,398 B1 | 5/2001 | Devane et al. |
| 6,248,359 B1 | 6/2001 | Faour |
| 6,248,363 B1 | 6/2001 | Patel et al. |
| 6,264,983 B1 | 7/2001 | Upadhyay |
| 6,274,173 B1 | 8/2001 | Sachs et al. |
| 6,303,146 B1 | 10/2001 | Bonhomme et al. |
| 6,309,663 B1 | 10/2001 | Patel et al. |
| 6,309,668 B1 | 10/2001 | Bastin et al. |
| 6,419,960 B1 | 7/2002 | Krishnamurthy et al. |
| 6,444,246 B1 | 9/2002 | Popplewell et al. |
| 6,472,373 B1 | 10/2002 | Albrecht |
| 6,475,521 B1 | 11/2002 | Timmins et al. |
| 6,566,560 B2 | 5/2003 | Travis |
| 6,576,260 B2 | 6/2003 | Bartholomaeus et al. |
| 6,627,635 B2 | 9/2003 | Palermo et al. |
| 6,630,171 B1 | 10/2003 | Huille et al. |
| 6,671,904 B2 | 1/2004 | Easterling |
| 6,692,768 B1 | 2/2004 | Ishibashi et al. |
| 6,696,088 B2 | 2/2004 | Oshlack et al. |
| 6,699,506 B1 | 3/2004 | Paillard et al. |
| 6,815,542 B2 | 11/2004 | Hong et al. |
| 6,846,810 B2 | 1/2005 | Martin et al. |
| 6,903,079 B2 | 6/2005 | Jagtap et al. |
| 6,946,146 B2 | 9/2005 | Mulye |
| 7,022,345 B2 | 4/2006 | Valducci et al. |
| 7,906,145 B2 | 3/2011 | Castan et al. |
| 8,445,023 B2 | 5/2013 | Guimberteau et al. |
| 8,652,529 B2 | 2/2014 | Guimberteau et al. |
| 9,023,400 B2 | 5/2015 | Guimberteau et al. |
| 2001/0000510 A1 | 4/2001 | Sakurai et al. |
| 2001/0006650 A1 | 7/2001 | Burnside et al. |
| 2001/0007680 A1 | 7/2001 | Kolter et al. |
| 2002/0068085 A1 | 6/2002 | Rudnic et al. |
| 2002/0068365 A1 | 6/2002 | Kuhrts |
| 2002/0197327 A1 | 12/2002 | Ulrich et al. |
| 2003/0050620 A1 | 3/2003 | Odidi et al. |
| 2003/0064108 A1 | 4/2003 | Lukas et al. |
| 2003/0068276 A1 | 4/2003 | Hughes et al. |
| 2003/0068371 A1 | 4/2003 | Oshlack et al. |
| 2003/0068392 A1 | 4/2003 | Sackler |
| 2003/0077297 A1 | 4/2003 | Chen et al. |
| 2003/0083286 A1 | 5/2003 | Teng et al. |
| 2003/0099711 A1 | 5/2003 | Meadows et al. |
| 2003/0104052 A1 | 6/2003 | Berner et al. |
| 2003/0104056 A1 | 6/2003 | Rudnic et al. |
| 2003/0118641 A1 | 6/2003 | Maloney et al. |
| 2003/0118654 A1 | 6/2003 | Santos et al. |
| 2003/0158242 A1 | 8/2003 | Kugelmann |
| 2003/0220399 A1 | 11/2003 | Luskey et al. |
| 2003/0224051 A1 | 12/2003 | Fink et al. |
| 2004/0010984 A1 | 1/2004 | Wright |
| 2004/0022849 A1 | 2/2004 | Castan et al. |
| 2004/0052731 A1 | 3/2004 | Hirsh et al. |
| 2004/0053887 A1 | 3/2004 | Obae et al. |
| 2004/0121015 A1 | 6/2004 | Chidlaw et al. |
| 2004/0121676 A1 | 6/2004 | Seko et al. |
| 2004/0126428 A1 | 7/2004 | Hughes et al. |
| 2004/0171584 A1 | 9/2004 | Millan et al. |
| 2004/0208936 A1 | 10/2004 | Chorin et al. |
| 2004/0228924 A1 | 11/2004 | Oshlack et al. |
| 2004/0234601 A1 | 11/2004 | Legrand et al. |
| 2005/0019406 A1 | 1/2005 | Kerrish et al. |
| 2005/0031546 A1 | 2/2005 | Bartholomaus et al. |
| 2005/0037077 A1 | 2/2005 | Legrand et al. |
| 2005/0059667 A1 | 3/2005 | Wolff |
| 2005/0089572 A1 | 4/2005 | Kumar et al. |
| 2005/0106248 A1 | 5/2005 | Dixit et al. |
| 2005/0106249 A1 | 5/2005 | Hwang et al. |
| 2005/0158392 A1 | 7/2005 | Kim et al. |
| 2005/0163856 A1 | 7/2005 | Maloney et al. |
| 2005/0181046 A1 | 8/2005 | Oshlack et al. |
| 2005/0214223 A1 | 9/2005 | Bartholomaeus et al. |
| 2005/0266078 A1 | 12/2005 | Jorda et al. |
| 2005/0281748 A1 | 12/2005 | Hirsh et al. |
| 2006/0039864 A1 | 2/2006 | Bartholomaus et al. |
| 2006/0099264 A1 | 5/2006 | Chan et al. |
| 2006/0165809 A1 | 7/2006 | Guimberteau et al. |
| 2007/0173464 A1 | 7/2007 | Guimberteau et al. |
| 2007/0183980 A1 | 8/2007 | Arkenau-Maric et al. |
| 2007/0196497 A1 | 8/2007 | Pouliquen et al. |
| 2007/0202049 A1 | 8/2007 | Guimberteau et al. |
| 2007/0224129 A1 | 9/2007 | Guimberteau et al. |
| 2007/0264326 A1 | 11/2007 | Guimberteau et al. |
| 2008/0008659 A1 | 1/2008 | Guimberteau et al. |
| 2008/0020018 A1 | 1/2008 | Moodley et al. |
| 2008/0193540 A1 | 8/2008 | Soula et al. |
| 2009/0041838 A1 | 2/2009 | Guimberteau et al. |
| 2011/0117205 A1 | 5/2011 | Castan et al. |
| 2014/0072644 A1 | 3/2014 | Guimberteau et al. |
| 2015/0313846 A1 | 11/2015 | Guimberteau et al. |
| 2015/0374635 A1 | 12/2015 | Castan et al. |
| 2015/0374636 A1 | 12/2015 | Castan et al. |

FOREIGN PATENT DOCUMENTS

| | | |
|---|---|---|
| DE | 2 417 465 A1 | 10/1975 |
| DE | 3943242 A1 | 6/1990 |
| EP | 0 005 129 A1 | 10/1979 |
| EP | 0 103 991 A2 | 3/1984 |
| EP | 0 166 287 A1 | 1/1986 |
| EP | 0 174 726 A1 | 3/1986 |

(56) References Cited

FOREIGN PATENT DOCUMENTS

| | | |
|---|---|---|
| EP | 0 179 023 A2 | 4/1986 |
| EP | 0198769 A2 | 10/1986 |
| EP | 0 202 027 A1 | 11/1986 |
| EP | 0 207 041 A2 | 12/1986 |
| EP | 0 213 563 A2 | 3/1987 |
| EP | 0 239 361 A1 | 9/1987 |
| EP | 0 249 587 A1 | 12/1987 |
| EP | 0 263 083 A1 | 4/1988 |
| EP | 0273890 | 7/1988 |
| EP | 0 281200 A1 | 9/1988 |
| EP | 0377518 | 7/1990 |
| EP | 0 383 967 A1 | 8/1990 |
| EP | 0 391 518 A2 | 10/1990 |
| EP | 0 411 590 A2 | 2/1991 |
| EP | 0 413 120 A2 | 2/1991 |
| EP | 0 477 135 A1 | 3/1992 |
| EP | 0475536 A1 | 3/1992 |
| EP | 0 502 642 A1 | 9/1992 |
| EP | 0 583 955 A2 | 2/1994 |
| EP | 0601508 | 6/1994 |
| EP | 0 609 961 A1 | 8/1994 |
| EP | 0624371 A1 | 11/1994 |
| EP | 0 647 448 A1 | 4/1995 |
| EP | 0709087 A1 | 5/1996 |
| EP | 0 721 776 A1 | 7/1996 |
| EP | 0734720 A1 | 10/1996 |
| EP | 0 793 959 A1 | 9/1997 |
| EP | 0 953 350 A1 | 11/1999 |
| EP | 0953359 A1 | 11/1999 |
| EP | 0 974 356 A1 | 1/2000 |
| EP | 1 062 955 A1 | 12/2000 |
| EP | 1 086 694 A2 | 3/2001 |
| EP | 1 101 490 A1 | 5/2001 |
| EP | 1123700 A1 | 8/2001 |
| EP | 1293209 A1 | 3/2003 |
| EP | 1 391 994 A2 | 2/2004 |
| FR | 2 313 915 A1 | 1/1977 |
| FR | 2634377 A1 | 1/1990 |
| FR | 2 670 112 A1 | 6/1992 |
| FR | 2 746 035 A1 | 9/1997 |
| FR | 2 759 083 A1 | 8/1998 |
| FR | 2 801 226 A1 | 5/2001 |
| FR | 2 811 571 A1 | 1/2002 |
| FR | 2 816 840 A1 | 5/2002 |
| FR | 2 830 447 A1 | 4/2003 |
| FR | 2 837 100 A1 | 9/2003 |
| FR | 2 840 614 A1 | 12/2003 |
| FR | 2 842 736 A1 | 1/2004 |
| FR | 2843117 A1 | 2/2004 |
| FR | 2 892 937 A1 | 5/2007 |
| FR | 2 897 267 A1 | 8/2007 |
| GB | 2 163 747 A | 3/1986 |
| GB | 2 202 143 A | 9/1988 |
| JP | H02121918 A | 5/1990 |
| JP | H032114 A | 1/1991 |
| JP | H07138164 A | 5/1995 |
| JP | H0873345 | 3/1996 |
| JP | H11139960 A | 5/1999 |
| JP | 2002-003366 A | 1/2002 |
| WO | WO-87/07833 A1 | 12/1987 |
| WO | WO-88/01213 A1 | 2/1988 |
| WO | WO-89/08449 A1 | 9/1989 |
| WO | WO-91/06286 A1 | 5/1991 |
| WO | WO-91/06287 A1 | 5/1991 |
| WO | WO-91/19711 A1 | 12/1991 |
| WO | WO-91/19712 A1 | 12/1991 |
| WO | WO-92/01446 A1 | 2/1992 |
| WO | WO-93/01805 A1 | 2/1993 |
| WO | WO-94/09762 A1 | 5/1994 |
| WO | WO-94/27988 A1 | 12/1994 |
| WO | WO-96/01628 A1 | 1/1996 |
| WO | WO-96/08243 A1 | 3/1996 |
| WO | WO-96/08277 A1 | 3/1996 |
| WO | WO-96/11675 A2 | 4/1996 |
| WO | WO-96/29991 A1 | 10/1996 |
| WO | WO-97/02810 A2 | 1/1997 |
| WO | WO-97/09042 A1 | 3/1997 |
| WO | WO-97/21436 A1 | 6/1997 |
| WO | WO-97/25066 A1 | 7/1997 |
| WO | WO-97/34584 A1 | 9/1997 |
| WO | WO-98/24411 A2 | 6/1998 |
| WO | WO-98/53680 A1 | 12/1998 |
| WO | WO-98/55107 A1 | 12/1998 |
| WO | WO-99/26608 A1 | 6/1999 |
| WO | WO-99/32091 A1 | 7/1999 |
| WO | WO-99/47125 A1 | 9/1999 |
| WO | WO-99/49846 A2 | 10/1999 |
| WO | WO-00/18374 A1 | 4/2000 |
| WO | WO-00/28989 A1 | 5/2000 |
| WO | WO-00/40233 A1 | 7/2000 |
| WO | WO-00/50015 A1 | 8/2000 |
| WO | WO-00/61116 A2 | 10/2000 |
| WO | WO-00/78293 A1 | 12/2000 |
| WO | WO-01/08661 A2 | 2/2001 |
| WO | WO-01/15682 | 3/2001 |
| WO | WO-01/21159 A2 | 3/2001 |
| WO | WO-01/32157 A2 | 5/2001 |
| WO | WO-01/32158 A2 | 5/2001 |
| WO | WO-01/37809 A1 | 5/2001 |
| WO | WO-01/58424 A1 | 8/2001 |
| WO | WO-02/39984 A2 | 5/2002 |
| WO | WO-02/053097 A2 | 7/2002 |
| WO | WO-02/066002 A2 | 8/2002 |
| WO | WO-02/072072 A2 | 9/2002 |
| WO | WO-02/094285 A2 | 11/2002 |
| WO | WO-03/013467 A1 | 2/2003 |
| WO | WO-03/013476 A1 | 2/2003 |
| WO | WO-03/013479 A1 | 2/2003 |
| WO | WO-03/013538 A1 | 2/2003 |
| WO | WO-03/020243 A1 | 3/2003 |
| WO | WO-03/030878 A2 | 4/2003 |
| WO | WO-03/033001 A1 | 4/2003 |
| WO | WO-03/035029 A1 | 5/2003 |
| WO | WO-03/035039 A1 | 5/2003 |
| WO | WO-03/077888 A2 | 9/2003 |
| WO | WO-03/082204 A2 | 10/2003 |
| WO | WO-03/084517 A2 | 10/2003 |
| WO | WO-03/084518 A2 | 10/2003 |
| WO | WO-03/094899 A1 | 11/2003 |
| WO | WO-03/094924 A1 | 11/2003 |
| WO | WO-03/103538 | 12/2003 |
| WO | WO-2004/004693 A1 | 1/2004 |
| WO | WO-2004/010983 A2 | 2/2004 |
| WO | WO-2004/010984 A2 | 2/2004 |
| WO | WO-2004/026262 A2 | 4/2004 |
| WO | WO-2004/035020 A2 | 4/2004 |
| WO | WO-2004/035090 A1 | 4/2004 |
| WO | WO-2004/037259 A1 | 5/2004 |
| WO | WO-2004/052346 A1 | 6/2004 |
| WO | WO-2004/054542 A2 | 7/2004 |
| WO | WO-2004/056337 A2 | 7/2004 |
| WO | WO-2004/064834 A1 | 8/2004 |
| WO | WO-2004/087175 A1 | 10/2004 |
| WO | WO-2005/009409 A2 | 2/2005 |
| WO | WO-2005/016313 A1 | 2/2005 |
| WO | WO-2005/016314 A1 | 2/2005 |
| WO | WO-2005/016370 A1 | 2/2005 |
| WO | WO-2005/079760 A1 | 9/2005 |
| WO | WO-2006/002886 A1 | 1/2006 |
| WO | WO-2006/044805 A2 | 4/2006 |
| WO | WO-2006/056712 A1 | 6/2006 |
| WO | WO-2006/056713 A1 | 6/2006 |
| WO | WO-2006/089843 A2 | 8/2006 |
| WO | WO-2006/125819 A2 | 11/2006 |
| WO | WO-2006/133733 A1 | 12/2006 |
| WO | WO-2006/134018 A2 | 12/2006 |
| WO | WO-2007/054378 A1 | 5/2007 |
| WO | WO-2007/093642 A2 | 8/2007 |

OTHER PUBLICATIONS

U.S. Appl. No. 12/638,739, filed Dec. 15, 2009, Florence Guimberteau et al.

(56) References Cited

OTHER PUBLICATIONS

U.S. Appl. No. 14/081,038, filed Nov. 15, 2013, Florence Guimberteau et al.
U.S. Appl. No. 10/510,643, filed May 23, 2005, Catherine Castan et al.
U.S. Appl. No. 14/014,137, filed Jan. 26, 2011, Catherine Castan et al.
U.S. Appl. No. 14/848,603, filed Sep. 9, 2015, Catherine Castan et al.
U.S. Appl. No. 14/698,147, filed Apr. 28, 2015, Florence Guimberteau et al.
In the U.S. Patent and Trademark Office, Non-Final Office Action in re: U.S. Appl. No. 10/996,780, dated Dec. 12, 2008, 18 pages.
In the U.S. Patent and Trademark Office, Office Action in re: U.S. Appl. No. 12/638,739, dated Feb. 9, 2012, 8 pages.
In the U.S. Patent and Trademark Office, Notice of Allowance in re: U.S. Appl. No. 12/638,739, dated Nov. 29, 2012, 7 pages.
In the U.S. Patent and Trademark Office, Notice of Allowance in re: U.S. Appl. No. 12/638,739, dated Mar. 4, 2013, 5 pages.
In the U.S. Patent and Trademark Office, Office Action in re: U.S. Appl. No. 14/081,038, dated Jan. 30, 2014, 11 pages.
In the U.S. Patent and Trademark Office, Final Office Action in re: U.S. Appl. No. 14/081,038, dated Oct. 21, 2014, 9 pages.
In the U.S. Patent and Trademark Office, Office Action in re: U.S. Appl. No. 14/081,038, dated May 7, 2015, 13 pages.
In the U.S. Patent and Trademark Office, Final Office Action in re: U.S. Appl. No. 14/081,038, dated Nov. 16, 2015, 4 pages.
In the U.S. Patent and Trademark Office, Notice of Allowance in re: U.S. Appl. No. 14/081,038, dated Mar. 14, 2016, 5 pages.
In the U.S. Patent and Trademark Office, Non-Final Office Action in re: U.S. Appl. No. 11/439,432, dated Jan. 30, 2009, 22 pages.
In the U.S. Patent and Trademark Office, Requirement for Restriction/Election in re: U.S. Appl. No. 11/439,432, dated Apr. 29, 2008, 13 pages.
In the U.S. Patent and Trademark Office, Office Action in re: U.S. Appl. No. 11/439,432, dated Jan. 30, 2009, 21 pages.
In the U.S. Patent and Trademark Office, Final Office Action in re: U.S. Appl. No. 11/439,432, dated Dec. 22, 2009, 12 pages.
In the U.S. Patent and Trademark Office, Office Action in re: U.S. Appl. No. 11/439,432, dated Jul. 13, 2011, 6 pages.
In the U.S. Patent and Trademark Office, Final Office Action in re: U.S. Appl. No. 11/439,432, dated Feb. 29, 2012, 10 pages.
In the U.S. Patent and Trademark Office, Office Action in re: U.S. Appl. No. 11/439,432, dated Dec. 7, 2012, 8 pages.
In the U.S. Patent and Trademark Office, Notice of Allowance in re: U.S. Appl. No. 11/439,432, dated Oct. 15, 2013, 11 pages.
In the U.S. Patent and Trademark Office, Notice of Allowance in re: U.S. Appl. No. 11/439,432, dated Nov. 12, 2013, 5 pages.
In the U.S. Patent and Trademark Office, Non-Final Office Action in re: U.S. Appl. No. 11/723,553, dated Oct. 4, 2007, 7 pages.
In the U.S. Patent and Trademark Office, Final Office Action in re: U.S. Appl. No. 11/723,553, dated Aug. 26, 2008, 11 pages.
In the U.S. Patent and Trademark Office, Non-Final Office Action in re: U.S. Appl. No. 10/332,463, dated Dec. 23, 2005, 6 pages.
In the U.S. Patent and Trademark Office, Final Office Action in re: U.S. Appl. No. 10/332,463, dated Sep. 21, 2006, 11 pages.
In the U.S. Patent and Trademark Office, Non-Final Office Action in re: U.S. Appl. No. 10/415,850, dated Mar. 28, 2006, 14 pages.
In the U.S. Patent and Trademark Office, Non-Final Office Action in re: U.S. Appl. No. 10/415,850, dated Feb. 18, 2009, 7 pages.
In the U.S. Patent and Trademark Office, Final Office Action in re: U.S. Appl. No. 10/415,850, dated Aug. 18, 2009, 8 pages.
In the U.S. Patent and Trademark Office, Non-Final Office Action in re: U.S. Appl. No. 10/826,690, dated Jul. 27, 2007, 13 pages.
In the U.S. Patent and Trademark Office, Final Office Action in re: U.S. Appl. No. 10/826,690, dated Jan. 7, 2009, 9 pages.
In the U.S. Patent and Trademark Office, Non-Final Office Action in re: U.S. Appl. No. 10/492,129, dated Jul. 26, 2007, 10 pages.
In the U.S. Patent and Trademark Office, Non-Final Office Action in re: U.S. Appl. No. 10/492,129 dated Sep. 8, 2008, 11 pages.
In the U.S. Patent and Trademark Office, Non-Final Office Action in re: U.S. Appl. No. 10/492,129, dated Apr. 29, 2009, 13 pages.
In the U.S. Patent and Trademark Office, Non-Final Office Action in re: U.S. Appl. No. 10/478,420, dated Sep. 30, 2008, 18 pages.
In the U.S. Patent and Trademark Office, Final Office Action in re: U.S. Appl. No. 10/478,420, dated Jul. 1, 2009, 27 pages.
In the U.S. Patent and Trademark Office, Non-Final Office Action in re: U.S. Appl. No. 10/507,886, dated Jul. 21, 2009, 11 pages.
In the U.S. Patent and Trademark Office, Non-Final Office Action in re: U.S. Appl. No. 10/510,621, dated Feb. 5, 2008, 13 pages.
In the U.S. Patent and Trademark Office, Final Office Action in re: U.S. Appl. No. 10/510,621, dated Mar. 30, 2009, 17 pages.
In the U.S. Patent and Trademark Office, Office Action in re: U.S. Appl. No. 13/014,137, dated Jul. 13, 2011, 12 pages.
In the U.S. Patent and Trademark Office, Final Office Action in re: U.S. Appl. No. 13/014,137, dated Dec. 16, 2011, 16 pages.
In the U.S. Patent and Trademark Office, Office Action in re: U.S. Appl. No. 13/014,137, dated Mar. 14, 2014, 15 pages.
In the U.S. Patent and Trademark Office, Final Office Action in re: U.S. Appl. No. 13/014,137, dated Nov. 26, 2014, 17 pages.
In the U.S. Patent and Trademark Office, Office Action in re: U.S. Appl. No. 13/014,137, dated Jul. 30, 2015, 34 pages.
In the U.S. Patent and Trademark Office, Office Action in re: U.S. Appl. No. 10/510,643, dated Feb. 5, 2008, 13 pages.
In the U.S. Patent and Trademark Office, Final Office Action in re: U.S. Appl. No. 10/510,643, dated Mar. 25, 2009, 19 pages.
In the U.S. Patent and Trademark Office, Office Action in re: U.S. Appl. No. 10/510,643, dated Dec. 7, 2009, 16 pages.
In the U.S. Patent and Trademark Office, Notice of Allowance in re: U.S. Appl. No. 10/510,643, dated Oct. 26, 2010, 8 pages.
In the U.S. Patent and Trademark Office, Non-Final Office Action in re: U.S. Appl. No. 10/522,252, dated Jan. 14, 2008, 10 pages.
In the U.S. Patent and Trademark Office, Final Office Action in re: U.S. Appl. No. 10/522,252, dated Aug. 19, 2008, 11 pages.
In the U.S. Patent and Trademark Office, Non-Final Office Action in re: U.S. Appl. No. 10/522,252, dated Jul. 6, 2009, 12 pages.
In the U.S. Patent and Trademark Office, Non-Final Office Action in re: U.S. Appl. No. 11/583,940, dated Mar. 3, 2008, 9 pages.
In the U.S. Patent and Trademark Office, Final Office Action in re: U.S. Appl. No. 11/583,940, dated Feb. 4, 2009, 13 pages.
In the U.S. Patent and Trademark Office, Non-Final Office Action in re: U.S. Appl. No. 11/583,940, dated Sep. 2, 2009, 11 pages.
In the U.S. Patent and Trademark Office, Non-Final Office Action in re: U.S. Appl. No. 10/522,234, dated Jan. 14, 2008, 11 pages.
In the U.S. Patent and Trademark Office, Non-Final Office Action in re: U.S. Appl. No. 08/544,208, dated Feb. 11, 1999, 7 pages.
In the U.S. Patent and Trademark Office, Non-Final Office Action in re: U.S. Appl. No. 08/753,013, dated Apr. 14, 1997, 4 pages.
In the U.S. Patent and Trademark Office, Requirement for Restriction/Election in re: U.S. Appl. No. 11/802,610, dated Jul. 9, 2008, 8 pages.
In the U.S. Patent and Trademark Office, Office Action in re: U.S. Appl. No. 11/802,610, dated Apr. 16, 2009, 8 pages.
In the U.S. Patent and Trademark Office, Office Action in re: U.S. Appl. No. 11/802,610, dated Nov. 16, 2009, 16 pages.
In the U.S. Patent and Trademark Office, Final Office Action in re: U.S. Appl. No. 11/802,610, dated May 18, 2010, 11 pages.
In the U.S. Patent and Trademark Office, Office Action in re: U.S. Appl. No. 11/802,610, dated Jul. 23, 2013, 16 pages.
In the U.S. Patent and Trademark Office, Final Office Action in re: U.S. Appl. No. 11/802,610, dated May 23, 2014, 19 pages.
In the U.S. Patent and Trademark Office, Final Office Action in re: U.S. Appl. No. 11/802,610, dated Aug. 26, 2014, 20 pages.
In the U.S. Patent and Trademark Office, Notice of Allowance in re: U.S. Appl. No. 11/802,610, dated Mar. 2, 2015, 12 pages.
In the U.S. Patent and Trademark Office, Non-Final Office Action in re: U.S. Appl. No. 11/802,610, dated Apr. 16, 2009, 9 pages.
In the U.S. Patent and Trademark Office, Non-Final Office Action in re: U.S. Appl. No. 11/648,605, dated Apr. 15, 2009, 15 pages.
In the U.S. Patent and Trademark Office, Non-Final Office Action in re: U.S. Appl. No. 11/651,577, dated Dec. 26, 2008, 23 pages.
In the U.S. Patent and Trademark Office, Final Office Action in re: U.S. Appl. No. 11/651,577, dated Jul. 31, 2009, 8 pages.

(56) References Cited

OTHER PUBLICATIONS

In the U.S. Patent and Trademark Office, Restriction/Election in re: U.S. Appl. No. 11/651,577, dated Apr. 9, 2011, 7 pages.
In the U.S. Patent and Trademark Office, Office Action in re: U.S. Appl. No. 11/651,577, dated Jan. 6, 2010, 7 pages.
In the U.S. Patent and Trademark Office, Final Office Action in re: U.S. Appl. No. 11/651,577, dated Jul. 9, 2010, 8 pages.
In the U.S. Patent and Trademark Office, Office Action in re: U.S. Appl. No. 11/651,577, dated Nov. 23, 2010, 13 pages.
In the U.S. Patent and Trademark Office, Final Office Action in re: U.S. Appl. No. 11/651,577, dated Apr. 29, 2011, 10 pages.
In the U.S. Patent and Trademark Office, Non-Final Office Action in re: U.S. Appl. No. 11/631,030, dated May 15, 2009, 5 pages.
In the U.S. Patent and Trademark Office, Restriction/Election in re: U.S. Appl. No. 11/791,336, dated Feb. 16, 2010, 6 pages.
In the U.S. Patent and Trademark Office, Office Action in re: U.S. Appl. No. 11/791,336, dated Jun. 23, 2010, 14 pages.
In the U.S. Patent and Trademark Office, Final Office Action in re: U.S. Appl. No. 11/791,336, dated Dec. 8, 2010, 7 pages.
Definition of the word "crush", [online], [retrieved on May 3, 2015]. Retrieved from the Internet: <URL: https://www.google.com/?gws_rd=ssl#q=crush+definition>.
Akiyoshi et al., "Stabilization of Insulin upon Supramolecular Complexation with Hydrophobized Polysaccharide Nanoparticle," *Chemistry Letters*, 1995; 8:707-08.
Amidon et al., "A Theoretical Basis for a Biopharmaceutic Drug Classification: The Correlation of in vitro Drug Product Dissolution and in vivo Bioavailability," *Pharmaceutical Research*, 1995; 12:413-20.
Becker et al., "Current Approaches to Prevent NSAID-Induced Gastropathy—COX Selectivity and Beyond," *British Journal of Clinical Pharmacology*, 2004; 58(6):587-600.
Candau, S., "Chapter 3: Light Scattering," *Surfactant Solutions*, vol. 22, Ed. R. Zana, M. Dekker, Inc., NY, 1984; pp. 147-207.
Catella-Lawson et al., "Cyclooxygenase Inhibitors and the Antiplatelet Effects of Aspirin," *New England Journal of Medicine*, 2001; 345(25):1809-17.
Committee for Proprietary Medicinal Products, "Note for Guidance on Quality of Modified Release Products: A: Oral Dosage Forms, B: Transdermal Dosage Forms, Section 1 (Quality), Annex 3: Similarity Factor f2," (1999) The European Agency for the Evaluation of Medicinal Products—Human Medicines Evaluation Unit, CPMP/QWP/604/96, pp. 1-15.
Constancis et al., "Macromolecular Colloids of Diblock Poly(amino acids) that Bind Insulin," *Journal of Colloid and Interface Science*, 1999; 217:357-368.
Davis et al., "The design and evolution of controlled release systems for the gastrointestinal tract", *J. Controlled Release*, 1985; 2:27-28.
Fuller, W.D., "A procedure for the facile synthesis of amino-acid n-carboxyanhydrides," *Biopolymers*, 1976;15:1869-71.
Gavrilin et al., "A Comparative Study of the Pharmacokinetics and Bioaccessibility of Potassium Losartan in Various Medicinal Forms," *Pharmaceutical Chemistry Journal*, 2002; 36(5):227-28.
Harada et al., "Formation of Polyion Complex Micelles in an Aqueous Milieu from a Pair of Oppositely-Charged Block Copolymers with Poly(ethylene glycol) Segments," *Macromolecules*, 1995; 28:5294-99.
Humphrey, M.J., "The Oral Bioavailability of Peptides and Related Drugs," *Delivery System for Peptide Drugs*, Plenum Press, 1986, pp. 139-151.
Jen et al., "Ribavirin dosing in chronic hepatitis C: Application of population pharmacokinetic-pharmacodynamic models," *Clin. Pharmacol. Ther.*, 2002; 72(4):349/61.
Kataoka, K. "Preparation of Novel Drug Carrier based on the Self-Association of Block Copolymer," *Drug Delivery System*, 1995; 10(5):363-70.
Kawana et al., Nucleoside Peptides. III. The Synthesis of N-[1-(9-Adenyl)-β-D-ribofuranuronosyl] Derivatives of Certain Amino Acids and Peptides, *J. Org. Chem.*, 1972; 37:288/91.
Kolter et al., BASF ExAct 2000; 5:4-5.

"Product Information, Losartan (potassium salt)," *Cayman Chemical*, 2005.
Qingshseng, "Release—Sustained Pellet of Ribavirin," XP002395861, 2004, *Chemical Abstracts*, Data Accession No. 2005:353828. (Abstract only).
Tao, X et al., "Preparation of Ribavirin Sustained—Release Pellets by Centrifugal Granulation Technology," XP002395860, 2005, *Chemical Abstracts*, Database accession No. 2005:500395. (Abstract only).
Torriani et al., "Peginterferon Alfa-2a plus Ribavirin for Chronic Hepatitis C Virus Infection in HIV-Infected Patients," *The New England Journal of Medicine* 351(5): 438-450 (2004).
Translation of the International Preliminary Examination Report for International Application No. PCT/FR2003/001096, completed Jul. 21, 2004.
Tsutsumiuchi et al., "Synthesis of Polyoxazoline-(Glyco)peptide Block Copolymer Ring-opening Polymerization of (Sugar-Substituted) α-Amino Acid N-Carboxyanhydrides with Polyoxazoline Macroinitiators," *Macromolecules*, 1997; 30:4013-17.
Volland Online Introductory Chemistry, 2005 , [online]. Retrieved from the Internet: <URL: www.800mainstreet.com/9/0009-004-solub.html>.
Yoshino, H., "Design and Evaluation of Time Controlled Release Systems for Site-Specific Oral Drug Delivery to the GI Tract," *Current Status on Targeted Drug Delivery to the GI Tract*, Capsugel Library, Symp. Ser. Short Hills 22/4, London 6/05, Tokyo 14/05, 1993; pp. 185-90.
Remington's The Science and Practice of Pharmacy, 1995, 19th edition, Mack Publishing Co. Pennsylvania, USA, vol. I, pp. 1-412.
Remington's The Science and Practice of Pharmacy, 1995, 19th edition, Mack Publishing Co. Pennsylvania, USA, vol. I, pp. 413—Glossary G5.
Remington's The Science and Practice of Pharmacy, 1995, 19th edition, Mack Publishing Co. Pennsylvania, USA, vol. II, pp. 1-1220.
Remington's The Science and Practice of Pharmacy, 1995, 19th edition, Mack Publishing Co. Pennsylvania, USA, vol. II, pp. 1221-1597.
Remington's The Science and Practice of Pharmacy, 1995, 19th edition, Mack Publishing Co. Pennsylvania, USA, vol. II, pp. 1598—Glossary G5.
U.S. Appl. No. 14/848,699, Office Action dated Oct. 19, 2016 in the U.S. Patent and Trademark Office.
Bauer et al., "Coated Pharmaceuticl Dosage Forms—Fundamentals, Manufacturing Techniques, Biopharmaceutical Aspects, Test Methods and Raw Materials," CRC Press, Scientific Publishers Stuttgart 1998, 5 pages.
Buri, P., "IV, Voie Orale," *Formes Pharmaceutiques Nouvelles Aspects Technologique, Biopharmaceutique, & Medical*, 1985, pp. 175-227. Including English Language translation and verification of translation dated Mar. 2017.
Definition of the word "granule", [online], [retrieved on May 3, 2015]. Retrieved from the Internet: <URL: http://www.merriam-webster.com/dictionary/granule>.
Dubernet, et al., "La microencapsulation: ses techniques et ses applications en biologie," (1986) L'actualité Chimique, pp. 19-28. Including English Language translation and verification of translation dated Mar. 2017.
Gao et al., "Measurement of the Binding of Proteins to Polyelectrolytes by Frontal Analysis Continuous Capillary Electrophoresis," *Anal. Chem.*, 1997; 69:2945-51.
Granberg et al., "Solubility of Paracetamol in Pure Solvents," Journal of Chemical and Engineering Data, 1999; 44:1391-1395.
Sandell, "Industrial Aspects of Pharmaceutics," Swedish Pharmaceutical Press, 1993.
International Search Report for International Application No. PCT/FR03/01096, dated Sep. 30, 2003.
U.S. Appl. No. 14/081,038, Final Office Action dated Jun. 7, 2017 in the U.S. Patent and Trademark Office.
U.S. Appl. No. 13/014,137, Final Office Action dated Oct. 13, 2016 in the U.S. Patent and Trademark Office.

\* cited by examiner

ORAL PHARMACEUTICAL FORMULATION IN THE FORM OF AQUEOUS SUSPENSION FOR MODIFIED RELEASE OF ACTIVE PRINCIPLE(S)

This application is a Continuation of U.S. application Ser. No. 13/014,137, filed Jan. 26, 2011, which is a Continuation of U.S. application Ser. No. 10/510,643, filed May 23, 2005, which is a National Phase of PCT Application No. PCT/FR03/01096, filed Apr. 7, 2003, which claims priority to French Application No. 02/04409, filed Apr. 9, 2002 and French Application No. 02/10847, filed Sep. 2, 2002, the entire disclosure of each are hereby incorporated by reference.

The invention relates to the field of the modified release of pharmaceutical active principles, excluding amoxicillin. In the present disclosure, the expression "modified release" arbitrarily denotes release of the active principle(s) which starts as soon as the galenical form is brought into contact with its dissolution medium (in vivo or in vitro) or release of the active principle(s) which does not start until after a predetermined period ranging e.g. from 0.5 to several hours. In terms of the invention, the time taken to release 50% of the active principle(s) is typically several hours and can extend e.g. from 0.5 to 30 hours.

More precisely, the invention relates to liquid pharmaceutical formulations for oral administration with the modified release of active principle(s), excluding amoxicillin. These formulations consist of suspensions or dispersions of microcapsules, each of which is formed of a core comprising amoxicillin and of a coating enveloping said core. According to the invention, the microcapsules constituting the disperse phase of the suspension are designed to allow the modified release of the active principle(s), excluding amoxicillin.

Even more particularly, the invention relates especially to "multimicrocapsular" aqueous suspensions of active principle(s) for oral administration, excluding amoxicillin, said suspensions being stable throughout the treatment and allowing the modified release of the active principle (excluding amoxicillin) These suspensions are of particular value in the case of:

forms for the modified release of active principles in high therapeutic doses (for example of 500 to 1000 milligrams or more);

liquid paediatric or geriatric forms for the modified release of active principles (for example sachets or reconstitutable oral suspensions in bottles);

taste masking and/or protection of sensitive active principles.

The invention further relates to a specific process for the preparation of the microcapsules to be suspended in water.

Oral pharmaceutical formulations for the modified release of active principle(s) are well known.

Some of these formulations consist of tablets comprising a therapeutically active core covered with various thicknesses of non-digestible materials.

Microcapsules or microspheres comprising a core of active principle(s) coated with layers of different permeability or solubility have appeared more recently. These microcapsules/microspheres are placed e.g. in gelatin capsules to form galenical systems for the modified release of active principle(s).

The majority of modified-release pharmaceutical forms that comprise a coated core of active ingredient(s) are presented in solid form: tablets, gelatin capsules, microspheres or microcapsules.

By way of illustration of microcapsules in the dry form, particular mention may be made of patent EP-B-0 709 087, . . . describes a (pharmaceutical or dietetic) galenical system, preferably in the form of a tablet, advantageously a disintegrating tablet, or in the form of a powder or gelatin capsule, characterized in that it comprises microcapsules of the reservoir type containing at least one medicinal and/or nutritional active principle (AP) selected especially from antibiotics, and intended for oral administration, characterized in that:

they consist of particles of AP each covered with a film coating of the following composition:

1—at least one film-forming polymer (P1) insoluble in the tract fluids, present in an amount of 50 to 90% by dry weight, based on the total weight of the coating composition, and consisting of at least one water-insoluble cellulose derivative, ethyl cellulose and/or cellulose acetate being particularly preferred;

2—at least one nitrogen-containing polymer (P2) present in an amount of 2 to 25% by dry weight, based on the total weight of the coating composition, and consisting of at least one polyacrylamide and/or poly-N-vinylamide and/or poly-N-vinyllactam, polyacrylamide and/or polyvinylpyrrolidone being particularly preferred;

3—at least one plasticizer present in an amount of 2 to 20% by dry weight, based on the total weight of the coating composition, and consisting of at least one of the following compounds: glycerol esters, phthalates, citrates, sebacates, cetyl alcohol esters, castor oil, salicylic acid and cutin, castor oil being particularly preferred;

4—and at least one surfactant and/or lubricant present in an amount of 2 to 20% by dry weight, based on the total weight of the coating composition, and selected from anionic surfactants, preferably alkali metal or alkaline earth metal salts of fatty acids, stearic and/or oleic acid being preferred, and/or from non-ionic surfactants, preferably polyethoxylated sorbitan esters and/or polyethoxylated castor oil derivatives, and/or from lubricants such as stearates, preferably calcium, magnesium, aluminium or zinc stearate, or stearylfumarate, preferably sodium stearylfumarate, and/or glycerol behenate, it being possible for said agent to comprise only one or a mixture of the above-mentioned products;

they have a particle size of between 50 and 1000 microns; and they are designed so as to be able to reside in the small intestine for a period of at least about 5 hours, thereby allowing the absorption of the AP during at least part of their residence time in the small intestine.

Said document relates only to dry pharmaceutical forms based on microcapsules and makes no mention of oral liquid pharmaceutical forms based on microcapsules.

These modified-release solid pharmaceutical formulations are not always advantageous, especially when they are administered to very young children or to very elderly patients with swallowing difficulties.

Such is the case when the active principles in question have to be administered orally in high doses, for example of 500 to 1000 milligrams or more, e.g. when the active principle is metformin. It is clear that such solid galenical systems are unsuitable because they are too bulky and hence very difficult to swallow, especially by young children or the elderly. This can be the cause of poor patient compliance and consequently jeopardize the success of the therapeutic treatment.

Likewise, in the case of paediatric forms, where the therapeutic dose has to be adapted according to the child's weight, the suspensions of the invention are suitable for the already existing bottles provided with syringes graduated in kg, and does not therefore necessitate the development of a novel device. The modified-release forms rarely employed hitherto for children are therefore now accessible by virtue of the invention. The advantages of such forms are the reduction in the number of daily dosage units and the optimization of the efficacy of the treatment between successive dosage units (e.g. for antibiotics, anti-inflammatories, cardiovascular treatments, etc.). Thus a controlled-release liquid pharmaceutical formulation which were easy to prepare would represent a significant advance.

In this case it would be even more advantageous to use modified-release galenical systems consisting of a plurality of microcapsules with a diameter of less than 1000 microns. In fact, in these systems, the dose of active principle(s) to be administered is distributed over a large number of microcapsules (typically 10,000 for a 500 mg dose) and thus has the following intrinsic advantages:

The use of a mixture of microcapsules with different modified-release profiles affords release profiles which have several release pulses or which, by appropriate regulation of the different fractions, ensure a constant plasma concentration level of the AP.

It avoids bringing the tissues into contact with a high dose of AP (dose dumping). Each microcapsule actually contains only a very reduced dose of active principle(s), thereby circumventing the risk of damage to the tissues due to a local overconcentration of aggressive active principle(s).

It is possible to combine several galenical forms (for immediate or modified release) containing one or more active principles in these "multimicrocapsular" systems.

Liquid multiparticulate galenical forms or, more precisely, colloidal suspensions are known which are preferred to the solid forms for oral administration in the case of high-dosage active principles or paediatric applications.

Liquid suspensions for the modified release of active principle(s) are difficult to produce. The main difficulty to be overcome is that of avoiding the release of the active principle(s) into the liquid phase during storage of the suspension, while allowing modified release as soon as it enters the gastrointestinal tract. This objective is particularly difficult to achieve because the active principle(s) is (are) stored in a liquid for a very long time compared with the desired release time in the gastrointestinal tract fluids. Furthermore, its prolonged residence in the liquid phase during storage must not perturb the modified-release system to the point of degrading the release profile and release time of the active principle(s).

Furthermore, for these liquid formulations to be fully effective, it is known to be important that:

the microcapsules are very small (<1000 microns),
and the weight fraction of coating excipients is limited, this modality being all the more difficult to achieve because, due to their small size, the microcapsules have a large specific surface area, accelerating the release.

As regards the prior art concerning oral liquid pharmaceutical forms for the modified release of active principles, French patent application FR-A-2 634 377 should be mentioned first of all; said document discloses a novel modified-release pharmaceutical form based on a resin/active principle complex coated with an ionic polymer whose polarity is opposite to that of the resin, and fixed thereto by ionic bonding. The active principle is also ionic and has a polarity opposite to that of the resin. The latter can be sodium polystyrenesulfonate and the ionic coating polymer is selected from acrylic and methacrylic acid ester polymers (EUDRAGIT®). The resin is impregnated with an aqueous solution of the active principle. The resin particles impregnated with active principle are then coated with an organic solution of ionic polymer. The resulting microcapsules can be converted to an oral suspension (Example 2 in particular). The use of an ionic resin and an ionic coating polymer limits the possible applications to ionic active principles.

American patents U.S. Pat. No. 4,999,189 and U.S. Pat. No. 5,186,930 relate to liquid pharmaceutical compositions comprising ion exchange ionic resin/active principle complexes suspended in a liquid phase. These particles of resin/active principle complex are coated with a first layer of pharmaceutically acceptable wax of high melting point and with a second, outer layer of a pharmaceutically acceptable water-insoluble polymer (ethyl cellulose, methyl cellulose, hydroxypropyl methyl cellulose, hydroxyethyl cellulose, Eudragit®, etc.). A plasticizer such as dibutyl sebacate can be introduced into this second, outer layer. The active principle is fixed by ionic bonding to the ion exchange resin. The liquid phase consists of a glucose syrup with a high fructose content and of several other ingredients such as glycerol or propylene glycol.

U.S. Pat. No. 5,186,930 differs from the first US patent in that it makes provision for a sufficient amount of the first layer (wax) to prevent the particles of resin/active principle complexes from swelling and crackling.

These US patents do not provide any data that allow the quality of the modified release of active principles to be assessed. Moreover, using ion exchange resins as the active principle support is rather inconvenient and restrictive in terms of the variety of active principles involved. Furthermore, this galenical system has nothing convincing to offer in terms of the stability and preservation of the modified-release properties of the active principle.

PCT patent application WO-A-87/07833 and patent U.S. Pat. No. 4,902,513 disclose aqueous suspensions of microcapsules of active principle (e.g. theophylline) with modified release of the active principle (e.g. 12 h). These suspensions are prepared by saturating the aqueous phase with the active principle before incorporating the microcapsules of active principle into this aqueous phase. The composition of the coating agent for the microcapsules that allows the modified release of the active principle is not described in said documents. Now, this coating composition is a decisive factor in guaranteeing the maintenance of the modified-release profile of the microcapsules after storage in the aqueous phase. The technical proposal described appears not to disclose the means of solving the dual problem of producing a liquid suspension of a modified-release microcapsular form without interfering with the stability of the modified-release profile of the active principle after the microcapsules have been stored in the liquid phase.

European patent application EP-A-0 601 508 relates to an aqueous suspension for the oral administration of naxopren according to a modified-release profile. This suspension comprises coated microgranules of naxopren suspended in a syrupy aqueous liquid phase. The technical problem underlying this invention is to provide a modified-release form of naxopren containing a 1000 mg dose and capable of administration in a single daily dosage unit.

The microgranules consist of naxopren, polyvinylpyrrolidone and lactose (90-300 μm). Their coating is made up of 4 layers. The first comprises diethyl cellulose/diethyl phthalate/polyethylene glycol. The second is based on EUDRAGIT (meth)acrylate/(meth)acrylic copolymers. The third comprises glycerol stearate/wax/fatty alcohols and the fourth consists of an enteric covering based on cellulose acetate/phthalate. The naxopren undergoes modified release over 24 hours.

Example 22 of said European patent application EP-A-0 601 508 contains a demonstration of the stability of the release profile after 30 days' storage of the liquid suspension.

One of the disadvantages of this suspension derives from the enteric layer, which prohibits the use of a suspension of neutral pH because this layer is designed to disintegrate and become liquid at neutral pH. Another disadvantage of this enteric layer is that it blocks the release of the active principle in the stomach at acidic pH. Now, for AP whose absorption window is situated in the upper parts of the gastrointestinal tract, it is often advantageous to release the active principle in the stomach in order to increase the bioavailability. Furthermore, this multilayer solution to the problem is very complex and in addition specific to naproxen.

PCT patent application WO-A-96/01628 discloses a liquid pharmaceutical formulation for the oral administration, according to a modified-release profile (12 hours), of an active principle consisting of moguisteine. The object is to propose a modified-release liquid formulation of moguisteine which is easy to measure out and ingest, has a release time that makes it possible to avoid multiple dosage units, is stable over time in aqueous suspension and is pleasantly flavoured in order to favour compliance, and whose manufacture does not involve the use of toxic substances like solvents. To achieve this object, the invention according to PCT patent application WO-A-96/01628 proposes a suspension, in a weakly hydrated liquid phase (essentially based on sorbitol and glycerol), of microgranules (90-300 μm) of moguisteine coated with a first, hydrophilic layer consisting of cellulose acetate/phthalate and diethyl phthalate, a second, hydrophobic layer containing glycerol stearate/wax/fatty alcohols, and a third, hydrophilic layer identical to the first.

This multilayer form is very complex to prepare and in addition is specific to moguisteine.

In this state of the art, the essential objective of the present invention is to propose an aqueous suspension of microcapsules of active principle(s), excluding amoxicillin, for the oral administration of the latter according to a modified-release profile, in which the coating of the microcapsules is designed in such a way that the release profile is not perturbed and does not depend on the maceration time of the microcapsules in the liquid (preferably aqueous) phase. Thus the active principle(s) contained in the microcapsules would be prevented from escaping into the liquid phase throughout the storage of the suspension, but a modified release of the active principle(s) would be allowed as soon as it entered an environment suitable for triggering the release, namely in vivo in the gastrointestinal tract and in vitro under the conditions of a dissolution test performed just after suspension of the microcapsules in the solvent (preferably aqueous) phase, using a type II apparatus according to the European Pharmacopoeia 3rd edition, in a phosphate buffer medium of pH 6.8, for a volume of 900 ml, at a temperature of 37° C.

Another objective of the present invention is to provide an aqueous liquid suspension of microcapsules of active principle(s) (excluding amoxicillin) comprising a film coating formed of a single layer.

Another objective of the present invention is to provide an aqueous liquid suspension of microcapsules of active principle(s) (excluding amoxicillin) in which the dissolved fraction originating from the microcapsules is less than or equal to 15% and preferably 5% of the total weight of active principles present in the microcapsules.

Another objective of the present invention is to provide an aqueous liquid suspension of microcapsules of active principle(s) (excluding amoxicillin) in which one part of the active principle(s) is in an immediate-release form and the other part of the active principle(s) is in a modified-release form (microcapsules).

Another essential objective of the present invention is to provide an aqueous suspension of microcapsules for the modified release of active principles (excluding amoxicillin) which makes it possible to release the active principle according to a release profile that is not degraded by the ageing of the suspension.

Another essential objective of the present invention is to provide an aqueous suspension of microcapsules which is made up of individually coated particles of active principle(s) (excluding amoxicillin) and makes it possible to release the latter according to a prolonged and/or optionally delayed profile such that the release half-life $t_{1/2}$ is between 0.5 and 30 hours.

Another objective of the present invention is to propose an oral galenical form which is liquid and consists of a large number (for example in the order of several thousands) of microcapsules, this multiplicity statistically ensuring a good reproducibility of the transit kinetics of the AP throughout the gastrointestinal tract, thereby improving control of the bioavailability and hence improving efficacy.

One essential objective of the present invention is to propose an oral liquid galenical form made up of a plurality of coated microcapsules which avoids the use of large amounts of coating agent, the weight fraction of coating agent being comparable to that of the monolithic forms.

Another essential objective of the present invention is to provide a modified-release aqueous suspension in which the active principle(s) (excluding amoxicillin) is (are) in the form of a plurality of particles individually coated to form microcapsules and allowing the mixing of several active principles having different respective release times.

Another essential objective of the present invention is to propose the use, as a means of treating human or veterinary diseases, of a (preferably aqueous) suspension of microcapsules consisting of particles of active principle(s) (excluding amoxicillin) individually coated so as to determine the modified release of the active principle(s) without the modified-release profile being affected by storage of the microcapsules in this liquid form in suspension.

Another essential objective of the present invention is to propose a drug based on a preferably aqueous suspension of microcapsules consisting of particles of active principle(s) (excluding amoxicillin) individually coated so as to determine the modified release of the active principle(s) without the modified-release profile being affected by storage of the microcapsules in this liquid form in suspension.

Having set themselves all the above objectives, among others, the inventors have succeeded in developing a multimicrocapsular galenical system in the form of a preferably aqueous suspension for the modified release of active principle(s), excluding amoxicillin, which:
    does not degrade the optionally retarded, modified-release profile,
    and is stable, easy to prepare, economic and effective.

To do this the inventors have proposed to:
select a totally specific coating composition for the microcapsules,
and suspend the microcapsules in a (preferably aqueous) liquid phase saturated with active principle(s) or capable of being saturated with active principle(s) on contact with the microcapsules, using an amount of solvent (preferably water) that is limited but nevertheless sufficient for the suspension to be easy to swallow.

Thus the invention which meets the objectives described above, among others, relates to a suspension of microcapsules in an aqueous liquid phase that allows the modified release of at least one active principle (excluding amoxicillin) and is intended for oral administration, characterized in that:
it comprises a plurality of microcapsules each consisting of a core containing at least one active principle (excluding amoxicillin) and of a film Coating that:
is applied to the core,
controls the modified release of the active principle(s),
and has a composition corresponding to one of the following three families A, B and C:
Family A
1A—at least one film-forming polymer (P1) insoluble in the tract fluids, present in an amount of 50 to 90 and preferably of 50 to 80% by dry weight, based on the total weight of the coating composition, and consisting of at least one water-insoluble cellulose derivative;
2A—at least one nitrogen-containing polymer (P2) present in an amount of 2 to 25 and preferably of 5 to 15% by dry weight, based on the total weight of the coating composition, and consisting of at least one polyacrylamide and/or poly-N-vinylamide and/or poly-N-vinyllactam;
3A—at least one plasticizer present in an amount of 2 to 20 and preferably of 4 to 15% by dry weight, based on the total weight of the coating composition, and consisting of at least one of the following compounds: glycerol esters, phthalates, citrates, sebacates, cetyl alcohol esters and castor oil;
4A—at least one surfactant and/or lubricant present in an amount of 2 to 20 and preferably of 4 to 15% by dry weight, based on the total weight of the coating composition, and selected from anionic surfactants and/or non-ionic surfactants and/or lubricants, it being possible for said agent to comprise only one or a mixture of the above-mentioned products;
Family B
1B—at least one hydrophilic polymer carrying groups ionized at neutral pH and preferably selected from cellulose derivatives;
2B—at least one hydrophobic compound different from A;
Family C
1C—at least one film-forming polymer insoluble in the gastrointestinal tract fluids;
2C—at least one water-soluble polymer;
3C—at least one plasticizer;
4C—optionally at least one surfactant/lubricant preferably selected from the following group of products:
anionic surfactants;
and/or non-ionic surfactants,
and the liquid phase is saturated or becomes saturated with active principle(s) on contact with the microcapsules.

In terms of the present disclosure, the expression "microcapsules of active principle(s)" denotes microcapsules whose core comprises one or more active principles and optionally at least one excipient.

This suspension according to the invention makes it possible to overcome the two main obstacles to the production of an aqueous suspension of microcapsules consisting of individually coated microparticles of active principles and allowing the modified release of the latter, these two obstacles being as follows:
a) limiting the fraction of active principles immediately releasable from the microcapsules to a value of less than 15% and preferably 5% of the total weight of active principles used in the microcapsules;
b) obtaining a modified-release system that is sufficiently robust to avoid any change or degradation of the release profile of the active principle(s) during storage of the aqueous suspension.

Also, this suspension makes it possible to facilitate the oral administration of drugs which have high therapeutic doses, especially in the case of the elderly and children, there being a significant gain in terms of compliance and success of the treatment.

Furthermore, for AP which have a limited absorption window, it is particularly advantageous for the modified-release form to be a plurality of microcapsules, as indicated in the preamble of the present disclosure.

In one preferred embodiment of the invention, the families A, B and C from which the constituents of the coating composition are selected are as follows:
Family A
1A—ethyl cellulose and/or cellulose acetate;
2A—polyacrylamide and/or polyvinylpyrrolidone;
3A—castor oil;
4A—an alkali metal or alkaline earth metal salt of fatty acids, stearic and/or oleic acid being preferred, a polyethoxylated sorbitan ester, a polyethoxylated castor oil derivative, a stearate, preferably calcium, magnesium, aluminium or zinc stearate, a stearylfumarate, preferably sodium stearylfumarate, or glycerol behenate, taken individually or in a mixture with one another;
Family B
1B
cellulose acetate-phthalate;
hydroxypropyl methyl cellulose phthalate;
hydroxypropyl methyl cellulose acetate-succinate;
(meth)acrylic acid/(meth)acrylic acid alkyl (methyl) ester copolymer (EUDRAGIT® S or L);
and mixtures thereof;
2B
hydrogenated vegetable waxes (Dynasan® P60, Dynasan® 116);
triglycerides (tristearin, tripalmitin, Lubritab®, Cutina HR, etc.);
animal and vegetable fats (beeswax, carnauba wax, etc.);
and mixtures thereof.
Family C
1C
water-insoluble cellulose derivatives, ethyl cellulose and/or cellulose acetate being particularly preferred;
acrylic derivatives;

polyvinyl acetates;
and mixtures thereof;

2C
water-soluble cellulose derivatives;
polyacrylamides;
poly-N-vinylamides;
poly-N-vinyllactams;
polyvinyl alcohols (PVA);
polyoxyethylenes (POE);
polyvinylpyrrolidones (PVP) (the latter being preferred);
and mixtures thereof;

3C
glycerol and its esters, preferably from the following subgroup: acetylated glycerides, glycerol monostearate, glyceryl triacetate and glycerol tributyrate;
phthalates, preferably from the following subgroup: dibutyl phthalate, diethyl phthalate, dimethyl phthalate and dioctyl phthalate;
citrates, preferably from the following subgroup: acetyltributyl citrate, acetyltriethyl citrate, tributyl citrate and triethyl citrate;
sebacates, preferably from the following subgroup: diethyl sebacate and dibutyl sebacate;
adipates;
azelates;
benzoates;
vegetable oils;
fumarates, preferably diethyl fumarate;
malates, preferably diethyl malate;
oxalates, preferably diethyl oxalate;
succinates, preferably dibutyl succinate;
butyrates;
cetyl alcohol esters;
salicylic acid;
triacetin;
malonates, preferably diethyl malonate;
cutin;
castor oil (this being particularly preferred);
and mixtures thereof;

4C
alkali metal or alkaline earth metal salts of fatty acids, stearic and/or oleic acid being preferred;
polyethoxylated oils, preferably polyethoxylated hydrogenated castor oil;
polyoxyethylene/polyoxypropylene copolymers;
polyethoxylated sorbitan esters;
polyethoxylated castor oil derivatives;
stearates, preferably calcium, magnesium, aluminium or zinc stearate;
stearylfumarates, preferably sodium stearylfumarate;
glycerol behenate;
and mixtures thereof.

Preferably, the film coating consists of a single layer whose weight represents from 1 to 50% and preferably from 5 to 40% of the total weight of the microcapsules.

According to one preferred characteristic of the invention, the liquid phase is aqueous; even more preferably, it contains at least 20% of water and preferably at least 50% by weight of water.

This suspension according to the invention advantageously contains:
30 to 95% by weight and preferably 60 to 85% by weight of liquid phase (advantageously water);
and 5 to 70% by weight and preferably 15 to 40% by weight of microcapsules.

Advantageously, the amount of solvent liquid phase (preferably water) for the active principle(s) (excluding amoxicillin) is such that the proportion of dissolved active principle(s) originating from the microcapsules is less than or equal to 15% and preferably less than or equal to 5% by weight, based on the total weight of the active principle(s) contained in the microcapsules.

In a first embodiment of the invention, the liquid phase is at least partially and preferably totally saturated with active principle(s) (excluding amoxicillin) following the incorporation of the microcapsules into this liquid phase.

In this embodiment, it is the active principle(s) contained in the microcapsules that saturate the liquid phase.

In a second embodiment of the invention, the liquid phase is at least partially and preferably totally saturated with active principle(s) (excluding amoxicillin) by means of non-encapsulated active principle(s) prior to the incorporation of the microcapsules into this liquid phase. This embodiment is of particular value for the administration of amoxicillin in that it makes it possible to combine an immediate-release fraction with a modified-release fraction.

In practice, this amounts to saturating the liquid phase with active principle(s) before the introduction of the microcapsules into the suspension, so that the active principle contained in the microcapsules plays no part, or virtually no part, in the saturation of the liquid phase. The diffusion of the active principle contained in the microcapsules is therefore suppressed or virtually suppressed.

According to one preferred characteristic of the invention enabling this liquid oral formulation to be fully effective, the microcapsules have a particle size less than or equal to 1000 microns, preferably of between 200 and 800 microns and particularly preferably of between 200 and 600 microns.

"Particle size" is understood in terms of the invention as meaning that a proportion of at least 75% by weight of microcapsules have a diameter between the screen size limits in question.

Again with the aim of improving efficacy, the amount of coating agent for the microcapsules advantageously represents from 1 to 50% and preferably 5 to 40% of the weight of the coated microcapsules. This advantageous characteristic is all the . . . to acquire because, due to their small size, the microcapsules have a large specific surface area, accelerating the release.

To control the in vivo in vitro release of the active principle(s), it is preferable according to the invention to use a film coating for the microcapsules which belongs to family A or C.

For more detailed qualitative and quantitative information on this coating composition of family A, reference may be made to European patent EP-B-0 709 087, the content of which forms part of the present disclosure by way of reference.

Another possible way of defining the liquid suspension according to the invention consists in considering an in vitro release profile obtained using a type II apparatus according to the European Pharmacopoeia 3rd edition, in a phosphate buffer medium of pH 6.8 and at a temperature of 37° C., such that:
the proportion PI of active principle(s) released from the microcapsules during the first 15 minutes of the dissolution test is such that:
PI≤15
preferably PI≤5;
the active principle(s) remaining in the microcapsules is (are) released over a period such that the release time of 50% by weight of AP ($t_{1/2}$) is defined as follows (in hours):

$0.5 \leq t_{1/2} \leq 30$ preferably $0.5 \leq t_{1/2} \leq 20$.

Still with regard to its in vitro dissolution properties, the suspension according to the invention is characterized in that:

the initial in vitro release profile Pfi obtained just after suspension of the microcapsules in the solvent (preferably aqueous) phase, using a type II apparatus according to the European Pharmacopoeia 3rd edition, in a phosphate buffer medium of pH 6.8, for a volume of 900 ml, at a temperature of 37° C., and the in vitro release profile $Pf_{10}$ obtained 10 days after suspension of the microcapsules in the solvent (preferably aqueous) phase, using a type II apparatus according to the European Pharmacopoeia 3rd edition, in a phosphate buffer medium of pH 6.8, at a temperature of 37° C., are similar.

The release profiles compared according to the recommendations of *The European Agency for the Evaluation of Medicinal Products (EMEA)—Human Medicines Evaluation Unit—/Committee for proprietary medicinal products (CPMP)—London, 29 Jul. 1999, CPMP/QWP/604/96: note for guidance on quality of modified release products: A: oral dosage forms, B: transdermal dosage forms—section I (quality)—Annex 3: Similarity factor* $f_2$, produce a value of >50 for the similarity factors $f_2$ and can therefore be declared similar.

These advantageous characteristics of the suspension according to the invention enable high doses of active principle(s) to be administered orally without difficulty and without detracting from the modified and optionally delayed release mode of the active principle.

According to another of its advantageous physicochemical characteristics, the pH of the liquid suspension according to the invention can arbitrarily be acidic or neutral.

It may be quite valuable to add at least one rheology modifier to the suspension. In particular, this can be one or more "viscosifiers" selected . . . those commonly employed in the pharmaceutical industry and especially those disclosed in *Handbook of pharmaceutical excipients—3rd edition, Am. Pharmaceutical Association,* Arthur H. KIBBE, 2000, ISBN 0917330-96-X Europe. 0-85369-381-1. Examples which may be mentioned are:

water-soluble cellulose derivatives (hydroxyethyl cellulose, hydroxypropyl cellulose, carboxymethyl cellulose, hydroxypropyl methyl cellulose, etc.);
polyethylene glycols;
alginates and derivatives thereof;
carrageenans;
agar-agar;
gelatin;
maltodextrins;
polydextrose;
guar, carob, acacia, xanthan, gellan and other gums;
polyvinyl alcohol;
povidone;
pectins;
silica gel;
native and modified starches and derivatives thereof;
dextrans;
etc.

It can also be advisable to introduce into the suspension at least one agent for modifying the solubility of the active principle in the solvent (preferably aqueous) liquid phase, for example salts, sugars, glycerol, etc. In fact, in the case of very soluble active principles, these solutes can limit the escape of the active principle from the microcapsules by lowering the saturation concentration of the active principle in the aqueous phase.

For the suspension to have all the qualities of an oral galenical form that is easy to swallow, stable and palatable, it advantageously contains at least one other additive selected from the group comprising surfactants, colourants, dispersants, preservatives, taste improvers, flavourings, sweeteners, antioxidants and mixtures thereof.

Examples of these additives which may be mentioned are those commonly employed in the pharmaceutical industry and especially those disclosed in *Handbook of pharmaceutical excipients—3rd edition, Am. Pharmaceutical Association,* Arthur H. KIBBE, 2000, ISBN 0917330-96-X Europe. 0-85369-381-1, or, in the case of emulsifiers, those described on page 5, lines 14 to 29, of EP-A-0 273 890, or again, in the case of thickeners, those indicated on page 5, lines 19 and 20, of EP-A-0 601 508.

The active principles used to prepare the controlled-release suspensions according to the invention can be selected from at least one of the following wide varieties of active substances: antiulcer drugs, antidiabetics, anticoagulants, antithrombics, hypolipidaemics, antiarrhythmics, vasodilators, antiangina drugs, antihypertensives, vasoprotectors, fertility promoters, labour inducers and inhibitors, contraceptives, antibiotics, antifungals, antivirals, anticancer drugs, anti-inflammatories, analgesics, antiepileptics, antiparkinsonism drugs, neuroleptics, hypnotics, anxiolytics, psychostimulants, antimigraine drugs, antidepressants, antitussives, antihistamines and antiallergics.

Without implying a limitation, the invention applies more particularly to pharmaceutical active principles which have to be administered orally in high doses, for example of 500 to 1000 milligrams or more, and to paediatric suspensions.

The active principle(s) is (are) preferably selected from the following compounds: pentoxifylline, prazosin, aciclovir, nifedipine, diltiazem, naproxen, ibuprofen, flurbiprofen, ketoprofen, fenoprofen, indomethacin, diclofenac, fentiazac, oestradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-asa, quinidine, perindopril, morphine, pentazocine, metformin, paracetamol, omeprazole, metoclopramide, atenolol, salbutamol morphine, verapamil, erythromycin, caffeine, furosemide, cephalosporins, montelukast, valaciclovir, ascorbic acid salts, diazepam, theophylline, ciprofloxacin, vancomycin, aminoglycosides, penicillins (except for amoxicillin) and mixtures thereof.

According to another of its features, the present invention relates to a drug, characterized in that it comprises a suspension of modified-release microcapsules of active principle(s), as defined above.

In more concrete terms, the invention further relates to a drug, or more exactly a galenical pack, characterized in that it comprises a kit for preparing the suspension as defined above, said kit containing:

microcapsules in substantially dry form containing the active principle(s) for saturating the liquid phase with active principle(s) once the two solid and liquid phases have been brought into contact;

and/or a mixture of microcapsules in substantially dry form containing the active principle(s) in the dose that is just necessary for modified release, together with immediate-release uncoated active principle(s) in a necessary and sufficient amount to saturate the liquid phase with active principle(s) once the saturation dose of active principle(s) and the liquid phase have been brought into contact;

and the liquid phase and/or at least part of the ingredients useful for its preparation, and/or the protocol for preparation of the suspension.

This type of presentation of the drug according to the invention enables patients easily to prepare the modified-release suspension in a form that is stable, particularly in terms of modified release, for at least several days. The patient is thus guaranteed to have a drug that is easy to administer orally and perfectly effective from the therapeutic point of view.

The microcapsules constituting the solid phase of the suspension according to the invention can be prepared by microencapsulation techniques available to those skilled in the art, the main techniques being summarized in the article by C. DLTVERNEY and J. P. BENOIT in "L'actualité chimique", December 1986. More precisely, the technique in question is microencapsulation by film coating, which yields individualized "reservoir" systems as opposed to matrix systems.

For further details, reference may be made to patent EP-B-0 953 359 cited above.

To produce the core based on active principle(s) (excluding amoxicillin) of the microcapsules according to the invention, it is advantageous to use, as starting materials, particles of active principle(s) of the desired size. Said particles can be crystals of active principle(s) which are pure and/or have undergone a pretreatment by one of the techniques conventionally employed in the art, for example granulation, in the presence of a small amount of at least one conventional binder and/or an agent for modifying the intrinsic solubility characteristics of the AP.

The invention will be understood more clearly from the point of view of its composition, properties and preparation with the aid of the Examples below, given solely by way of illustration, which demonstrate the variants and the advantages of the invention.

EXAMPLE 1

Preparation of Microcapsules of Aciclovir 1000 g of aciclovir and 30 g of Povidone® are mixed dry for 5 minutes. The mixture is granulated with water. The granules are dried at 40° C. in a ventilated oven and then graded on a 500 μm screen. The 200-500 μm fraction is selected.

700 g of granules obtained above are coated with 27.3 g of ethyl cellulose, 3.7 g of castor oil, 3.7 g of magnesium stearate and 2.9 g of Povidone® dissolved in a 60/40 w/w acetone/isopropanol mixture, in a Glatt GPC-G1 fluidized air bed apparatus. Temperature of product: 40° C.

Preparation of the Suspension:

0.58 g of microcapsules obtained above is placed in 37 ml of phosphate buffer of pH 6.8.

Test:

The above suspension is stored for 10 days at room temperature. After 10 days the suspension is analysed for dissolution using a type II apparatus according to the European Pharmacopoeia 3rd edition, phosphate buffer medium of pH 6.8, volume of 900 ml, temperature of 37° C., blade stirring at 100 rpm, UV detection at 252 nm.

Figure 1:
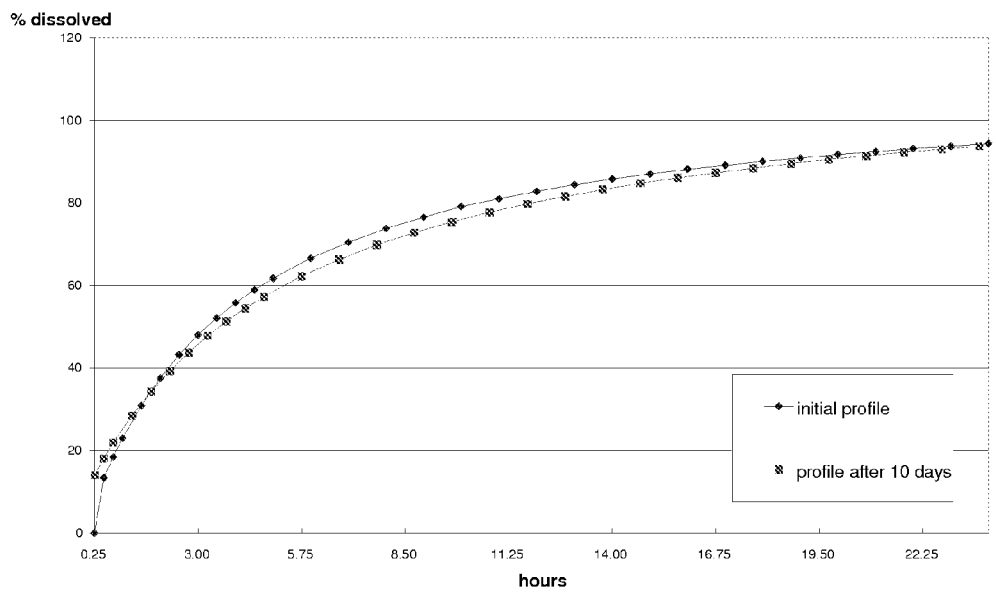
FIG. 1 shows the initial dissolution profile and the dissolution profile after 10 days' storage of the suspension according to Example 1, in % dissolved (D) as a function of the time (t) in hours.

The result is shown in FIG. 1 attached.

The profiles are apparently identical: similarity factor $f_2$ greater than 50. The microcapsules remain highly effective in aqueous suspension.

EXAMPLE 2

Preparation of Microcapsules of Spironolactone

Step 1: Granules 45 g of spironolactone, 25 g of PEG 40-hydrogenated castor oil and 30 g of povidone are first solubilized in a water/acetone/isopropanol mixture (5/57/38 w/w). This solution is then sprayed onto 800 g of cellulose spheres (of diameter between 300 and 500 Dm) in a Glatt GPC-G1 fluidized air bed apparatus.

Step 2: Coating 50 g of granules obtained above are coated with 1.44 g of ethyl cellulose, 0.16 g of castor oil, 0.64 g of poloxamer 188 and 0.96 g of povidone dissolved in an acetone/isopropanol mixture (60/40 w/w), in a miniGlatt fluidized air bed apparatus.

Preparation of the Suspension:

0.07 g of microcapsules obtained above is placed in 0.165 ml of phosphate buffer of pH 6.8.

Test:

The above suspension is stored for 19 days at room temperature. After 19 days the suspension is analysed for dissolution using a type II apparatus according to the European Pharmacopoeia 3rd edition, phosphate buffer medium of pH 6.8, volume of 1000 ml, temperature of 37° C., blade stirring at 100 rpm, UV detection at 240 nm.

Figure 2:
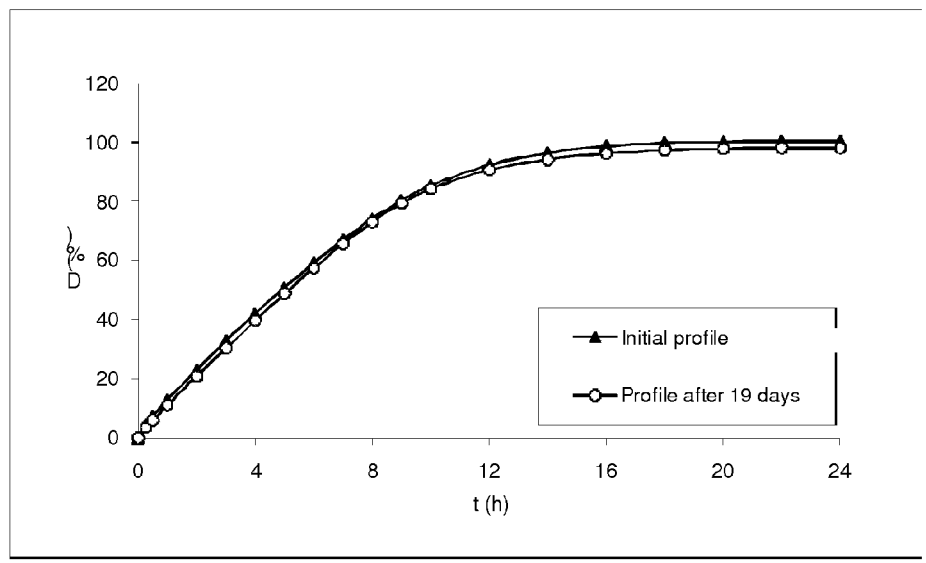
FIG. 2 shows the initial dissolution profile and the dissolution profile after 19 days' storage of the suspension according to Example 2, in % dissolved (D) as a function of the time (t) in hours.

The result is shown in FIG. 2 attached.

The profiles are apparently identical: similarity factor $f_2$ greater than 50. The microcapsules remain very effective in aqueous suspension.

EXAMPLE 3

Preparation of Microcapsules of Metformin 740 g of metformin crystals (200-500 μm fraction) are coated with 192.4 g of ethyl cellulose, 26 g of castor oil, 26 g of magnesium stearate and 20.8 g of Povidone® dissolved in a 60/40 w/w acetone/isopropanol mixture, in a Glatt GPC-G1 fluidized air bed apparatus. Temperature of product: 40° C.

Preparation of the Suspension (29% of Free Form and 71% of Encapsulated Form):

50 g of microcapsules obtained above are mixed dry with 15 g of metformin crystals and 0.7 g of xanthan gum in a 100 ml glass flask. 34.3 g of purified water are then added to the powder mixture. After manual stirring, a suspension is obtained which produces a sediment very slowly.

The total metformin titre in the suspension is 0.52 g/ml.

Stability Test:

The above suspension is stored for 12 days at room temperature. After 12 days the suspension is analysed for dissolution using a type II apparatus according to the European Pharmacopoeia 3rd edition, phosphate buffer medium of pH 6.8, volume of 900 ml, temperature of 37° C., blade stirring at 100 rpm, UV detection at 232 nm.

Figure 3:
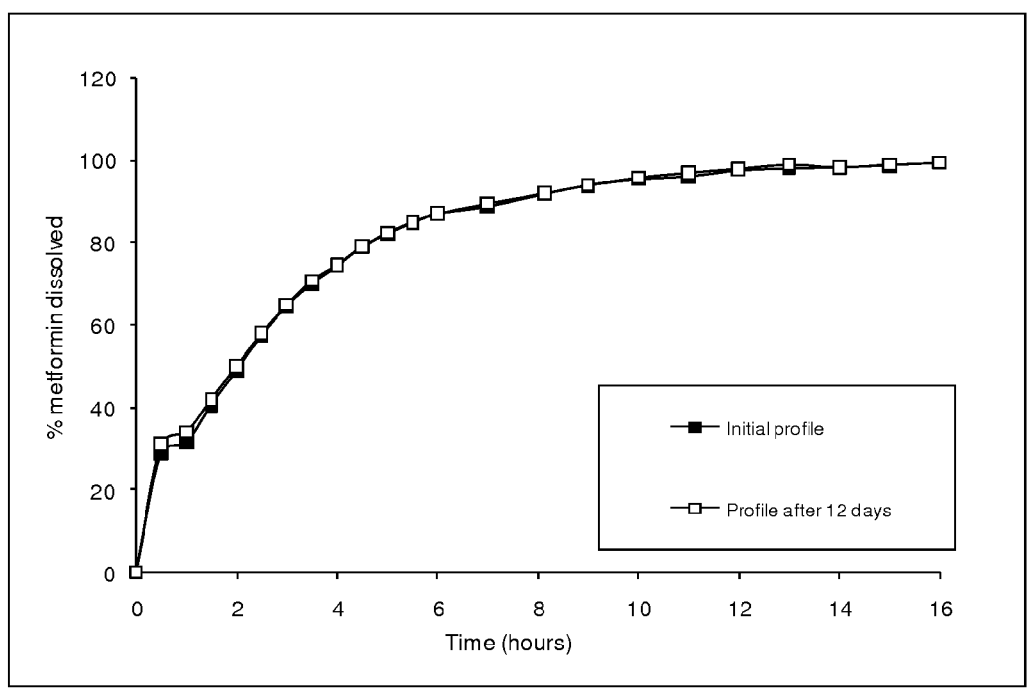
FIG. 3 shows the initial dissolution profile and the dissolution profile after 12 days' storage of the suspension according to Example 3, in % dissolved (D) as a function of the time (t) in hours. This suspension combines 29% of free metformin with 71% of encapsulated metformin.

The result is shown in FIG. 3 attached.

The profiles are apparently identical: similarity factor $f_2$ greater than 50. The microcapsules remain very effective in aqueous suspension.

Homogeneity Test:

The above suspension is stirred manually and then six 5 ml samples are taken with a graduated syringe. The metformin content of each sample is determined by HPLC and is shown below:

| Sample no. | Metformin content for 5 ml of suspension (in g) |
| --- | --- |
| 1 | 2.58 |
| 2 | 2.60 |
| 3 | 2.62 |
| 4 | 2.59 |
| 5 | 2.60 |
| 6 | 2.63 |

It is seen that the samples are very homogeneous and that the dosage corresponds to the expected value of 2.60 g for 5 ml.

This formulation can therefore be administered without risk of overdosing or underdosing.

The invention claimed is:

1. A method comprising:
    orally administering a suspension of microcapsules to a patient, wherein the suspension of microcapsules comprises a plurality of microcapsules and an aqueous liquid phase, and wherein each microcapsule comprises:
        (a) a core comprising at least one active principle, wherein the at least one active principle is not amoxicillin; and
        (b) a film coating applied to the core, wherein the film coating comprises:
            (1) at least one film-forming polymer (P1) insoluble in gastrointestinal tract fluids, present in an amount of 50 to 90% by dry weight based on the total weight of the coating composition, and wherein at least one of said at least one film-forming polymer (P1) is a water-insoluble cellulose derivative;
            (2) at least one nitrogen-containing polymer (P2) present in an amount of 2 to 25% by dry weight based on the total weight of the coating composition, and wherein at least one of said at least one nitrogen-containing polymer (P2) is selected from the group consisting of: polyacrylamide, poly-N-vinylamide, and poly-N-vinyllactam;
            (3) at least one plasticizer present in an amount of 2 to 20% by dry weight based on the total weight of the coating composition, and wherein at least one of said at least one plasticizer is selected from the group consisting of: glycerol esters, phthalates, citrates, sebacates, cetyl alcohol esters, and castor oil; and
            (4) at least one surfactant or lubricant present in an amount of 2 to 20% by dry weight based on the total weight of the coating composition, and wherein at least one of said at least one surfactant or lubricant is selected from the group consisting of: anionic surfactants, non-ionic surfactants, and lubricants, and mixtures thereof,
    wherein the film coating provides modified release of the at least one active principle in gastrointestinal fluids,
    wherein the aqueous liquid phase is saturated or becomes saturated with the at least one active principle on contact with the microcapsules, and
    wherein the in vitro release profile of the suspension of microcapsules in an aqueous liquid phase on day ten is similar to the release profile on day zero, as measured using a type II apparatus according to the European Pharmacopoeia 3rd edition, in a phosphate buffer medium of pH 6.8, at a temperature of 37° C.

2. The method of claim 1, wherein the film coating comprises:
    the at least one film-forming polymer (P1) present in an amount of 50 to 80% by dry weight based on the total weight of the coating composition;
    the at least one nitrogen-containing polymer (P2) present in an amount of 5 to 15% by dry weight based on the total weight of the coating composition;
    the at least one plasticizer present in an amount of 4 to 15% by dry weight based on the total weight of the coating composition; and
    the at least one surfactant or lubricant present in an amount of 4 to 15% by dry weight based on the total weight of the coating composition.

3. The method of claim 1, wherein each microcapsule has only one coating layer.

4. The method of claim 1, wherein the suspension of microcapsules comprises 30 to 95% by weight of liquid phase; and 5 to 70% by weight of microcapsules.

5. The method of claim 4, wherein the suspension of microcapsules comprises 60 to 85% by weight of liquid phase.

6. The method of claim 4, wherein the suspension of microcapsules comprises 15 to 40% by weight of microcapsules.

7. The method of claim 1, wherein a proportion of dissolved at least one active principle originating from the plurality of microcapsules is less than or equal to 15% by weight of the total weight of the at least one active principle contained in the plurality of microcapsules.

8. The method of claim 7, wherein a proportion of dissolved at least one active principle originating from the plurality of microcapsules is less than or equal to 5% by weight of the total weight of the at least one active principle contained in the plurality of microcapsules.

9. The method of claim 1, wherein the at least one active principle contained in the plurality of microcapsules saturates the aqueous liquid phase.

10. The method of claim 1, wherein the aqueous liquid phase is at least partially saturated with active principle by non-encapsulated active principle prior to the incorporation of the plurality of microcapsules into the aqueous liquid phase.

11. The method of claim 1, wherein the plurality of microcapsules have a particle size less than or equal to 1000 microns.

12. The method of claim 11, wherein the plurality of microcapsules have a particle size between 200 and 800 microns.

13. The method of claim 12, wherein the plurality of microcapsules have a particle size between 200 and 600 microns.

14. The method of claim 1, wherein 1 to 50% of the total weight of the coated microcapsules is film coating.

15. The method of claim 14, wherein 5 to 40% of the total weight of the coated microcapsules is film coating.

16. The method of claim 1, wherein the in vitro release profile of the suspension of microcapsules, as measured using a type II apparatus according to the European Pharmacopoeia 3rd edition, in a phosphate buffer medium of pH 6.8, at a temperature of 37° C., is such that the proportion, PI, of the at least one active principle released during the first 15 minutes of the dissolution test is not greater than 15%, and the remaining at least one active principle is released over a period such that the release time of 50% by weight of active principle ($t_{1/2}$) is not lower than 0.5 hour and not greater than 30 hours.

17. The method of claim 16, wherein the proportion, PI, of the at least one active principle released during the first 15 minutes of the dissolution test is not greater than 5%, and the remaining at least one active principle is released over a period such that the release time of 50% by weight of active principle ($t_{1/2}$) is not lower than 0.5 hour and not greater than 20 hours.

18. The method of claim 1, wherein the pH of the suspension of microcapsules is acidic or neutral.

19. The method of claim 1, wherein the suspension of microcapsules further comprises at least one rheology modifier.

20. The method of claim 19, wherein the at least one rheology modifier is xanthan.

21. The method of claim 19, wherein the at least one rheology modifier is carboxymethylcellulose.

22. The method of claim 1, wherein the suspension of microcapsules further comprises at least one agent for modifying the solubility of the at least one active principle in the aqueous liquid phase.

23. The method of claim 1, wherein the suspension of microcapsules further comprises at least one additive selected from the group consisting of: surfactants, colorants, dispersants, preservatives, taste improvers, flavorings, sweeteners, antioxidants, and mixtures thereof.

24. The method of claim 1, wherein the suspension further comprises at least one additional active principle in an immediate release form.

25. The method of claim 1, wherein the aqueous liquid phase comprises at least 20% by weight of water.

26. The method of claim 1, wherein the aqueous liquid phase comprises at least 50% by weight of water.

27. The method of claim 1, wherein:
at least one of the at least one film-forming polymer (P1) is selected from the group consisting of ethylcellulose and cellulose acetate;
at least one of the at least one nitrogen-containing polymer (P2) is selected from the group consisting of polyacrylamide and polyvinylpyrrolidone;
at least one of the at least one plasticizer is castor oil; and
the at least one surfactant or lubricant is selected from the group consisting of anionic surfactants, non-ionic surfactants and lubricants and mixtures thereof.

28. The method of claim 27, wherein:
at least one of the at least one film-forming polymer (P1) is ethylcellulose;
at least one of the at least one nitrogen-containing polymer (P2) is polyvinylpyrrolidone;
at least one of the at least one plasticizer is castor oil; and
at least one of the at least one surfactant or lubricant is selected from the group consisting of: an alkali metal salt of fatty acids, stearic acid, oleic acid, a polyethoxylated sorbitan ester, a polyethoxylated castor oil derivative, a stearate, a stearylfumarate, sodium strearlyfumarate, glycerol behenate, and mixtures thereof.

29. The method of claim 1, wherein the at least one active principle is selected from the group consisting of: antiulcer drugs, antidiabetics, anticoagulants, antithrombics, hypolipidaemics, antiarrhythmics, vasodilators, antiangina drugs, antihypertensives, vasoprotectors, fertility promoters, labor inducers and inhibitors, contraceptives, antibiotics, antifungals, antivirals, anticancer drugs, anti-inflammatories, analgesics, antiepileptics, antiparkinsonism drugs, neuroleptics, hypnotics, anxiolytics, psychostimulants, antimigraine drugs, antidepressants, antitussives, antihistamines, antiallergics, and mixtures thereof.

30. The method of claim 29, wherein the at least one active principle is selected from the group consisting of: pentoxifylline, prazosin, aciclovir, nifedipine, diltiazem, naproxen, ibuprofen, flurbiprofen, ketoprofen, fenoprofen, indomethacin, diclofenac, fentiazac, oestradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-asa, quinidine, perindopril, morphine, pentazocine, metformin, paracetamol, omeprazole, metoclopramide, atenolol, salbutamol morphine, verapamil, erythromycin, caffeine, furosemide, cephalosporins, montelukast, valaciclovir, ascorbic acid salts, diazepam, theophylline, ciprofloxacin, vancomycin, aminoglycosides, penicillins, and mixtures thereof.

31. The method of claim 30, wherein the at least one active principle is ibuprofen.

* * * * *